(12) United States Patent
Toomey et al.

(10) Patent No.: US 10,206,862 B2
(45) Date of Patent: Feb. 19, 2019

(54) SUPPLEMENT TO SUPPORT HEALTHY HAIR, SKIN, AND NAILS

(71) Applicant: New Chapter, Inc., Cincinnati, OH (US)

(72) Inventors: Jennifer Marie Toomey, Greenfield, MA (US); Paul Schulick, Brattleboro, VT (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/700,208

(22) Filed: Sep. 11, 2017

(65) Prior Publication Data

US 2018/0071191 A1   Mar. 15, 2018

Related U.S. Application Data

(60) Provisional application No. 62/393,381, filed on Sep. 12, 2016.

(51) Int. Cl.

| | | |
|---|---|---|
| *A61K 8/67* | (2006.01) | |
| *A61K 8/96* | (2006.01) | |
| *A61Q 19/08* | (2006.01) | |
| *A61K 8/35* | (2006.01) | |
| *A61Q 3/00* | (2006.01) | |
| *A61Q 5/00* | (2006.01) | |
| *A61Q 19/00* | (2006.01) | |
| *A61K 31/122* | (2006.01) | |
| *A61K 31/4188* | (2006.01) | |
| *A61K 36/074* | (2006.01) | |
| *A61K 8/9706* | (2017.01) | |
| *A61K 8/9728* | (2017.01) | |
| *A61K 36/05* | (2006.01) | |

(52) U.S. Cl.
CPC ............... *A61K 8/673* (2013.01); *A61K 8/35* (2013.01); *A61K 8/96* (2013.01); *A61K 8/9706* (2017.08); *A61K 8/9728* (2017.08); *A61K 31/122* (2013.01); *A61K 31/4188* (2013.01); *A61K 36/05* (2013.01); *A61K 36/074* (2013.01); *A61Q 3/00* (2013.01); *A61Q 5/00* (2013.01); *A61Q 19/00* (2013.01); *A61Q 19/08* (2013.01); *A61K 2800/92* (2013.01)

(58) Field of Classification Search
None
See application file for complete search history.

(56) References Cited

U.S. PATENT DOCUMENTS

| | | |
|---|---|---|
| 2004/0071752 A1 | 4/2004 | Hornack et al. |
| 2004/0241114 A1 | 12/2004 | Gupta |
| 2009/0306222 A1* | 12/2009 | Burton .................. A23K 20/174 514/763 |
| 2014/0357576 A1 | 12/2014 | Breuille et al. |
| 2016/0376263 A1* | 12/2016 | Patron .................. C07D 413/14 514/784 |

FOREIGN PATENT DOCUMENTS

| | | |
|---|---|---|
| CA | 2831083 A1 | 10/2012 |
| CA | 2907667 A1 | 10/2014 |
| CN | 103599137 A | 2/2014 |
| CN | 104839659 A | 8/2015 |
| CN | 104855983 A * | 8/2015 |
| GB | 2494475 A | 3/2013 |
| IN | 3088DEL2011 | 5/2016 |
| WO | WO2002100329 A2 | 12/2002 |

OTHER PUBLICATIONS

Dore et al. 2006 (Haematococcus algae meal as a source of natural astaxanthin for aquaculture feeds; Cyanotech Corporation publication; May 12, 2006) (Year: 2006).*
Paterson et al. 2006 (Ganoderma—A therapeutic fungal biofactory; Phytochemistry 67: 1985-2001). (Year: 2006).*
Soo 1996 (Effective Dosage of the Extract of Ganoderma lucidum in the Treatment of Various Aliments; in Mushroom Biology and Mushroom Products, Royse (ed.) Penn State University; ISBN 1-883956-01-3) (Year: 1996).*
Park et al. 2010 (Astaxanthin decreased oxidative stress and inflammation and enhanced immune response in humans; Nutrition and Metabolism 7:18) (Year: 2010).*
Vesely 1982 (Biotin Enhances Guanylate Cyclase Activity; Science 216:1329) (Year: 1982).*
Search Report and Written Opinion for PCT/US2017/050907 dated Nov. 29, 2017.
Collagen Plus Skin Essentials Liquicaps GNPD SOLAL Technologies, South Africa Oct. 2013.
Dietary Supplement without Iron and Iodine—GNPD—General Nutrition Corporation—GNC—USA—Jan. 2013.
GNC Womens Ultra Mega 50 Plus Multivitamin—GNPD—USA—Jun. 2007.
GNC_Mega_Men_Sport_Dietary_Supplement—GNPD—South Africa, 2015.
GNC_WellBeing_BeWhole_Premium-Multivitamin_and_Mineral_Dietary_Supplement_for_Women—GNPD—USA, Nov. 2009.
GNC_Womens_Ultra_Mega_Dietary_Supplement—GNPD—South Africa, Jul. 2015.
Jivesse Marine Collagen Capsules—GNPD, Clinidirect, UK, Nov. 2014.
Nativa, Premium Multi-Nutrient Supplement, South Africa, 2013—GNPD.
Natures_Plus_AgeLoss_Mens_Multi_Dietary_Supplement—GNPD—Hong Kong Sep. 2015.
New Chapter Dietary Supplement—Database GNPD (Online) Mintel; Sep. 2014, Database accession No. 2662857.

(Continued)

*Primary Examiner* — Mary Maille Lyons
(74) *Attorney, Agent, or Firm* — Amanda Herman

(57) ABSTRACT

A supplement composition formulated to support the health of a human's hair skin and nails containing biotin, *Haematococcus pluvialis* algae, and Reishi.

9 Claims, 3 Drawing Sheets

(56) References Cited

OTHER PUBLICATIONS

New Chapter Skin, Hair and Nails Food Supplement—Database GNPD—Nov. 2011—Database accession No. 1676088.
Sentosa_Senior_Multivitamins_and_Multiminerals_Tablets—GPND—Taiwan—Feb. 2015.
Supplements Men's Mega Men—GNPD—General Nutrition Corporation—GNC—Dietary Supplements—India, Feb. 2011.
Total Skin and Body Supplements—GNPD—NV Perricone MD Cosmeceuticale, UK, Mar. 2013.
Vitamex—Vitamin Supplement—GNPD—Spain, Mar. 2010.
Whole Food Multivitamin Tablets for Soothing Stress Support—Database GNPD (Online) Mintel, Sep. 2011, database accession No. 1614021.

\* cited by examiner

SUPPLEMENT TO SUPPORT HEALTHY HAIR, SKIN, AND NAILS

FIELD OF THE INVENTION

This invention relates to a supplement, particularly a supplement that supports healthy hair, skin, and nails.

BACKGROUND OF THE INVENTION

Practicing good nutrition is challenging. Some people seek supplements to provide additional nutrients to improve their health and wellness, including the growth of healthy, strong nails, healthy shiny hair, and healthy clear skin. In particular, consumers want to look and feel beautiful on the inside and out. However, some consumers complain about dry and/or brittle hair, skin, and/or nails; uneven skin tone and texture; shiny, oily, blotchy, and/or itchy skin; dull, fine, and/or thinning hair; and weak nails.

Thus, there remains a need for a supplement composition that supports healthy hair, skin, and nails.

SUMMARY OF THE INVENTION

A supplement composition formulated to support the health of a human's hair skin and nails comprising a daily intake comprising: (a) about 225 µg to about 750 µg biotin; (b) about 75 mg to about 250 mg *Haematococcus pluvialis* algae wherein the *Haematococcus pluvialis* algae comprises at least 4 mg astaxanthin per daily intake; (c) about 50 mg to about 500 mg Reishi.

A supplement composition formulated to support the health of a human's hair skin and nails comprising a daily intake comprising: (a) at least 300 µg of biotin per daily intake; (b) at least 120 mg of *Haematococcus pluvialis* algae per daily intake; (c) and at least 100 mg Reishi.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
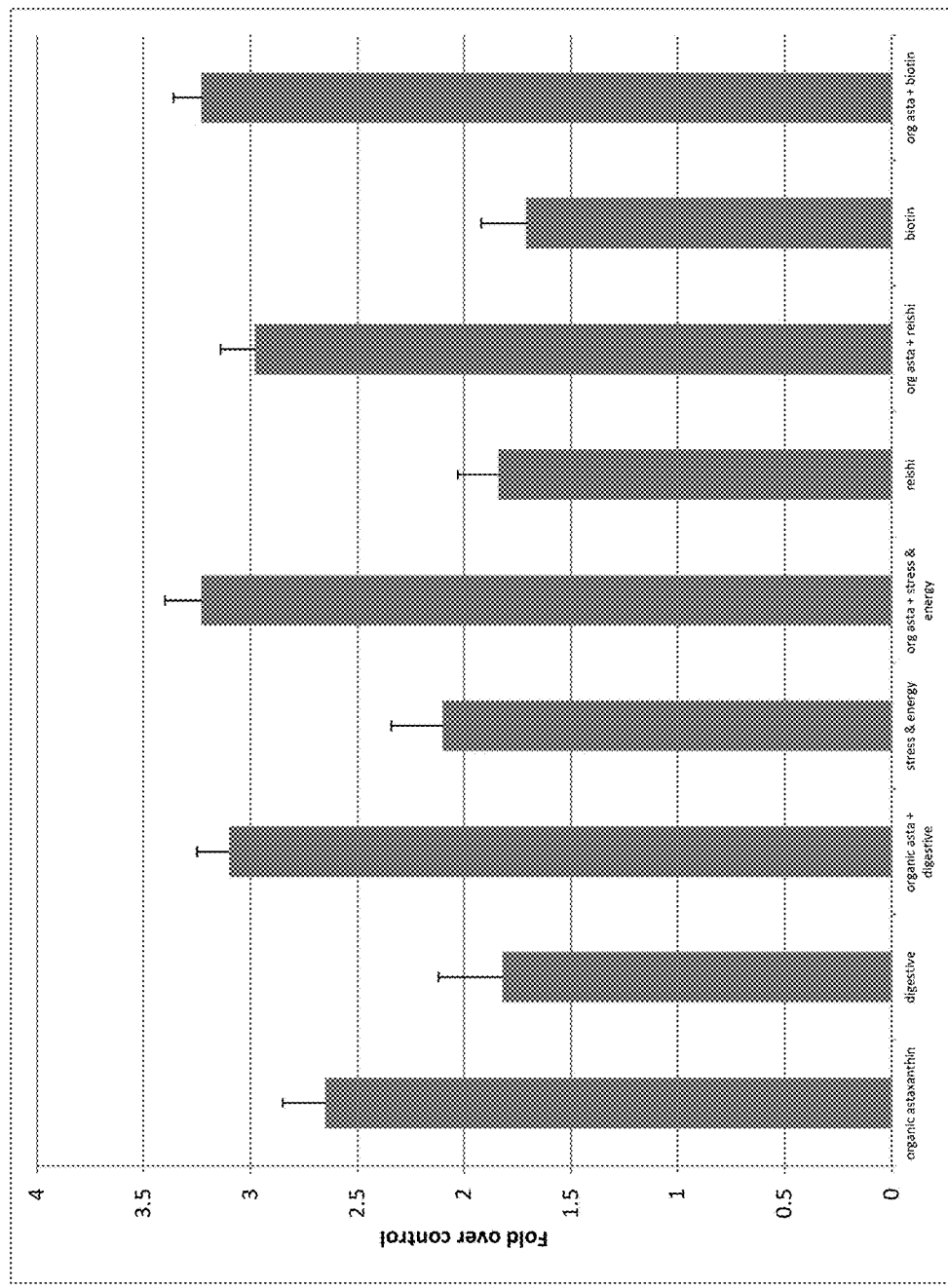
FIG. 1 shows components and combinations of components that activate the Biological Antioxidant Response Nrf2.

The main function of the skin is to act as a physical, chemical, and antimicrobial defense system. However, aging can impact longevity of cell membranes and stress and poor digestion can also impact the health of hair, skin, and nails. Studies have shown that stress and gut inflammation can impair the integrity and protective function of the epidermal barrier, which decreases the antimicrobial peptides produced in the skin and can cause an increase in the severity of infection and inflammation of the skin. Furthermore, stress can cause a chemical response in one's body that makes skin more sensitive and reactive and can also slow healing. Nutrition and exposure to UV radiation can play a role in skin, hair, and nail health and appearance. Because the external environment is constantly changing and the body is constantly reacting to the effects of aging and stress the processes associated hair, skin, and nails maintenance may benefit from supplements to help maintain its homeostasis.

Some consumers may desire a supplement to provide additional nutrients to help support the health of her hair, skin and nails. In particular, consumers may be looking for a supplement that can reduce fine lines and/or wrinkles, improve skin elasticity, maintain a youthful appearance, and/or support healthy immune function. This can be achieved by selecting ingredients, in particular herbal ingredients, that can target multiple biological pathways. In some examples, the supplement can be a non-GMO supplement that can contain organic ingredients.

In one example, the supplement can contain at least 300 µg of biotin, at least 120 mg of organic *Haematococcus pluvialis* algae, and at least 100 mg organic Reishi (*Ganoderma lucidum*, Ling zhi) (mycelium and fruiting bodies) per daily intake. The *Haematococcus pluvialis* algae can contain astaxanthin, in particular at least 4 mg astaxanthin per daily intake. The supplement can further contain a botanical blend for stress and energy support and/or digestive support. The botanical blend can be from culture media. The botanical blend for stress and energy support can contain organic schizandra (berry), organic maca (root), and/or organic chamomile (flower). In one example, the supplement can contain at least about 75 mg of the botanical blend for stress and energy support per daily intake. The botanical blend for digestive support can contain organic aloe (leaf), organic peppermint (leaf), organic coriander (seed), organic cardamom (seed), and/or organic artichoke (leaf). In another example, the supplement can contain at least about 50 mg of the botanical blend for digestive support per daily intake. The supplement can be in any suitable dosage form including a two piece capsule that can contain pullulan (*Auerobasidium pullalans*), carrageenan, water, and potassium chloride. The supplement can also contain organic brown rice and culture media.

As used herein, the terms "administer," "administering," and "administration," refer to any method which, in sound medical practice, delivers the supplement to a subject in such a manner as to provide a therapeutic effect.

As used herein, the term "non-GMO" means that the product has been verified as fully compliant to the Non-GMO Project Standard. Meets the standards of the non-GMO Project Standard as of May 21, 2014, and thus the product can be labeled Non-GMO Project Verified.

As used herein, the term "organic" means that the ingredient complies with International Certification Services, Inc. (ICS) organic guidelines (available Sep. 12, 2016) which states that the ingredient needs to be at least 70% organic.

As used herein, the terms "hydroalcoholic extraction" or "hydroethanolic extraction" refer to the technique in which hydrophilic compounds can be extracted from a sample utilizing a solution of alcohol and water, followed by evaporation of the solution to produce an extract consisting of dissolved solids. In the case of hydroethanolic extraction, the alcohol is ethanol.

As used herein, the term "supercritical fluid" refers to a gas that is heated to a temperature critical point, over which the gas will maintain its gaseous state and not turn to a liquid regardless of pressure. A gas heated to a temperature above its critical point will become very dense on compression, so that its characteristics resemble those of a liquid, but will not become liquid. Carbon dioxide is commonly used in applications requiring a supercritical fluid. The general properties of supercritical fluids and the general use of supercritical fluids in extraction processes are described in, e.g. Taylor, Supercritical Fluid Extraction, Wiley, 1996; McHugh and Krukonis, Supercritical Fluid Extraction: Principles and Practice, 2nd ed., Butterworth-Heinemann, 1994; and Williams and Clifford, Supercritical Fluid Methods and Protocols, Humana Press, 2000.

As used herein, the term "supercritical extraction" refers to the technique in which hydrophobic compounds can be extracted from samples utilizing a supercritical fluid. The solvation power of a supercritical fluid is increased as the pressure and temperature are increased above their critical points, producing an effective solvent for the isolation of hydrophobic molecules.

As used herein, the term "supplement" refers to a supplement intended to supplement a diet of food and water, where the diet is sufficient to support life. A supplement may contain vitamins, minerals, herbs or other botanicals, amino acids, enzymes, organ tissues, glandular metabolites, or combinations thereof. A supplement may be an extract or concentrate of a particular food source or a particular nutrient. Supplements may be administered by any convenient means, including parenteral or enteral routes. Enteral routes may include oral, gastric, or subgastric administration, including rectal administration.

As used herein, the term "vegetarian" refers to a product, including but not limited to foods and supplements, which are not made from or with the aid of products derived from animals that have died, have been slaughtered, or animals that die as a result of being eaten. Animals means farmed, wild or domestic animals, including, but not limited to, livestock poultry, game, fish, shellfish, crustacea, amphibians, tunicates, echinoderms, mollusks and insects. In one example, a product can be vegetarian if it includes dairy products and eggs.

As used herein, the term "vegan" refers to a product including, but not limited to foods and supplements, which are not made from or with the aid of animals or animal products (including products from living animals).

In a preferred form, the supplements of the present invention are administered orally. Oral administration dosage forms include, without limitation, tablets, capsules, softgels, gelcaps, liquids, powders, and films, as well as food-like forms such as bars, candies, lozenges, beverages, and the like. In one example, the supplement can be a capsule. In one example, the capsule can be a two piece capsule and in another example the capsule can be vegetarian.

As used herein, the articles "a" and "an" are understood to mean one or more of the material that is claimed or described, for example, "an active ingredient" or "a supplement".

The supplement can contain, consist of, or consist essentially of, the essential elements and limitations of the invention described herein, as well as any additional or optional ingredients, components, or limitations described herein or otherwise useful in supplements intended for use or consumption by humans.

In one example, the supplement can contain biotin (vitamin $B_7$). Biotin can help support the health of the skin, nerves, digestive track, metabolism, and cells. In one example, the biotin can be cultured. In one example, the supplement can contain from about 50 µg to about 10,000 µg biotin per daily intake, in another example from about 100 µg to about 5,000 µg, in another example from about 150 µg to about 2,500 µg, in another example from about 200 µg to about 1000 µg, in another example from about 225 µg to about 750 µg, in another example from about 275 µg to about 600 µg, in another example from about 290 µg to about 500 µg, and in another example from about 300 µg to about 400 µg. In another example, the supplement can contain at least 100 µg biotin per daily intake, in another example at least 200 µg, in another example at least about 300 µg, in another example at least about 600 µg, in another example at least about 1,000 µg, and in another example at least about 5000 µg. In another example the supplement can contain less than about 5,000 µg biotin per daily intake, in another example less than about 1,000 µg, and in another example less than about 700 µg.

In one example, the supplement can contain *Haematococcus pluvialis* algae. In one example at least a portion of the *Haematococcus pluvialis* can be organic and in another example all of the *Haematococcus pluvialis* can be organic. In another example, the supplement can contain from about 10 mg to about 1000 mg *Haematococcus pluvialis* per daily intake. In another example from about 30 mg to about 750 mg, in another example from about 60 mg to about 500 mg, in another example from about 50 mg to about 300 mg, in another example from about 75 mg to about 250 mg, in another example from about 90 mg to about 200 mg, in another example from about 100 mg to about 160 mg, in another example from about 105 mg to about 140 mg, and in another example from about 110 mg to about 130 mg. In another example, the supplement can contain at least about 50 mg *Haematococcus pluvialis* per daily intake, in another example at least about 75 mg, in another example at least about 100 mg, in another example at least about 120 mg, and in another example at least about 150 mg. In another example the supplement can contain less than about 500 mg *Haematococcus pluvialis* per daily intake, in another example less than about 300 mg, in another example less than about 200 mg.

In one example, the supplement can contain astaxanthin. Astaxanthin is an antioxidant and sometimes referred to as a strong antioxidant. It can help support a variety of health benefits, including skin benefits and increasing circulation as well as providing antioxidant activity against free radicals. In one example, the supplement can contain *Haematococcus pluvialis* algae which can contain astaxanthin. In another example, the supplement can contain an extract containing astaxanthin. In one example, the supplement can contain from about 1 mg to about 15 mg astaxanthin per daily intake, in another example about from 1.5 mg to about 12 mg, in another example from about 2 mg to about 10 mg, in another example from about 2.5 mg to about 8 mg, in another example from about 3 mg to about 7 mg, in another example from about 3.5 mg to about 6 mg, and in another example from about 4 mg to about 5 mg. In another example, the supplement can contain at least 2 mg astaxanthin per daily intake, in another example at least 3 mg, in another example at least 4 mg, and in another example at least 5 mg. In another example the supplement can contain less than 15 mg astaxanthin per daily intake, in another example less than 12 mg, and in another example less than 7 mg.

In one example, the supplement can contain Reishi mushroom (*Ganoderma lucidum*, Ling zhi). Some examples contain Reishi, an herbal mushroom. Reishi can support the immune system, in part due to beta-glucans present in the cell walls of the mushroom. The supplement can include any portion of the Reishi mushroom including the fruiting body (above-ground part), mycelium (filaments connecting a group of mushrooms), and/or spores. In one example at least a portion of the Reishi mushroom can be organic and in another example the Reishi mushroom can be organic. Reishi mushroom can support anti-aging, longevity, and immunity. The supplement can contain from about 10 mg to about 1500 mg Reishi mushroom per daily intake, in another example from about 20 mg to about 1200 mg, in another example from about 30 mg to about 1000 mg, in another example from about 40 mg to about 700 mg, in another example from about 50 mg to about 500 mg, in another example from about 60 mg to about 200 mg, in another example from about 70 mg to about 170 mg, in another example from about 80 mg to about 150 mg, and in another example from about 90 mg to about 120 mg. In another example, the supplement can contain at least 50 mg Reishi mushroom per daily intake, in another example at least 75 mg, in another example at least 100 mg, and in another example at least 150 mg. In another example, the supplement can contain less than 1200 mg Reishi mushroom per daily intake, in another example less than 1000 mg, in another example less than 600 mg, in another example less than 500 mg, and in another example less than 300 mg.

In another example the supplement can contain Vitamin A In one example, the supplement can contain at least 5,000 IU Vitamin A per daily intake and in another example at least 6000 IU.

In another example, the supplement can contain Vitamin C In one example, the supplement can contain at least 60 mg Vitamin C per daily intake and in another example at least 90 mg.

In another example, the supplement can contain Vitamin D In one example, the supplement can contain at least 800 IU Vitamin D per daily intake, in another example at least 600 IU, in another example at least 400 IU, and in another example at least 200 IU.

In another example, the supplement can contain Vitamin E In one example, the supplement can contain at least 15 IU Vitamin E per daily intake and in another example at least 30 IU and in another example at least 60 IU.

In another example, the supplement can contain thiamin (Vitamin $B_1$). In one example, the supplement can contain at least 5 mg thiamin per daily intake.

In another example, the supplement can contain riboflavin (Vitamin $B_2$). In one example, the supplement can contain at least 5 mg riboflavin per daily intake.

In another example, the supplement can contain niacin (Vitamin $B_3$). In one example, the supplement can contain at least 25 mg niacin per daily intake and in another example at least 18 mg.

In another example, the supplement can contain Vitamin $B_6$. In one example, the supplement can contain at least 5 mg Vitamin $B_6$ per daily intake and in another example at least 3 mg.

In another example, the supplement can contain folic acid (Vitamin $B_9$). In one example, the supplement can contain at least 200 µg niacin per daily intake.

In another example, the supplement can contain pantothenic acid (Vitamin $B_5$). In one example, the supplement can contain at least 15 mg pantothenic acid per daily intake and in another example at least 120 µg.

In one example, the supplement can contain iodine. In one example, the supplement can contain at least 120 µg iodine per daily intake.

In another example, the supplement can contain iron. In one example, the supplement can contain at least 3 mg iron per daily intake.

In another example, the supplement can contain zinc. In one example, the supplement can contain at least 7.5 mg zinc per daily intake.

In another example, the supplement can contain selenium. In one example, the supplement can contain at least 12.5 µg selenium per daily intake.

In another example, the supplement can contain manganese. In one example, the supplement can contain at least 5 mg manganese per daily intake.

In another example, the supplement can contain argan oil (*Argania spinosa*). In one example, the supplement can contain 25 mg argan oil per daily intake.

In another example, the supplement can contain PABA (Para-Aminobenzoic Acid). In one example the supplement can contain at least 10 mg PABA per daily intake.

In another example, the supplement can contain choline bitartrate. In one example, the supplement can contain at least 10 mg choline bitartrate per daily intake.

In another example, the supplement can contain alpha lipoic acid. In one example, the supplement can contain at least 10 mg alpha lipoic acid per daily intake.

In another example, the supplement can contain horsetail (*Equisetum arvense*). In one example, the supplement can contain at least 3 mg horsetail per daily intake.

In another example, the supplement can contain collagen, for instance hydrolyzed collagen. In one example, the supplement can contain at least 50 mg collagen per daily intake, in another example at least 100 mg, in another example at least 250 mg, in another example at least 500 mg, in another example at least 1000 mg, in another example at least about 2000 mg, in another example at least 5000 mg, and in another example at least 6500 mg.

In another example, the supplement can contain hyaluronic acid. In one example, the supplement can contain at least 30 mg hyaluronic acid per daily intake.

In some examples, the supplement can also contain one or more botanicals. In one example, the botanicals can be ingredients can be whole-food cultured. In one example, the supplement can contain one or more botanicals to provide stress and/or energy support and the botanicals can be selected from the group consisting of schizandra, maca, organic chamomile (flower), and combinations thereof. In another example, the supplement can contain one or more botanicals for digestive support selected from the group consisting of aloe, peppermint, coriander, cardamom, artichoke, and combinations thereof.

In one example the supplement can contain ginger (rhizome). In one example, the supplement can contain a hydroethanolic extract of ginger and/or a supercritical extract of ginger. In another example, the supplement can contain a ginger rhizome. In one example, the supplement can contain from about 10 mg to about 300 mg ginger per daily intake, in another example from about 50 mg to about 250 mg ginger, in another example from about 100 mg to about 200 mg ginger, in another example from about 125 mg to about 175 mg ginger, and in another example from about 140 mg to about 160 mg. In another example the supplement can contain from about 1 mg to about 25 mg ginger per daily intake, in another example from about 2 mg to about 15 mg, in another example 3 mg to about 7 mg. In another example the supplement can contain from about 0.5 mg to about 8 mg hydroethanolic extract of ginger per daily intake, in another example from about 1 mg to about 7 mg, and in another example from about 2 mg to about 4 mg. In another example, the supplement can contain from about 20 mg to about 160 mg of a hydroethanolic extract of ginger per daily intake, in another example from about 40 mg to about 130 mg, in another example from about 60 mg to about 120 mg, and in another example from about 75 mg to about 110 mg. In another example, the supplement can contain from about 10 mg to about 100 mg supercritical extract of ginger per daily intake, in another example from about 30 mg to about 75 mg, and in another example from about 40 mg to about 65 mg. In another example the supplement can contain from about 0.1 mg to about 5 mg supercritical extract of ginger per daily intake, in another example from about 0.2 mg to about 3 mg, in another example from about 0.3 mg to about 1 mg, and in another example from about 0.4 mg to about 0.8 mg.

In another example the supplement can contain turmeric (rhizome). In one example, the supplement can contain turmeric powder and/or a supercritical extract of turmeric and/or hydroethanolic extract. In one example, the supplement can contain from about 50 mg to about 750 mg turmeric per daily intake, in another example from about 100 mg to about 600 mg, in another example from about 200 mg to about 550 mg, in another example from about 300 mg to about 500 mg, and in another example from about 350 mg to about 450 mg. In another example, the supplement can contain from about 5 mg to about 50 mg turmeric per daily intake, in another example from about 10 mg to about 45 mg, in another example from about 20 mg to about 40 mg, and in another example from about 25 mg to about 45 mg. In another example, the supplement can contain from about 1 mg to about 20 mg supercritical extract of turmeric per daily intake, in another example from about 3 mg to about 15 mg, and in another example from about 5 mg to about 12 mg. In another example, the supplement can contain from about from about 100 mg to about 500 mg hydroethanolic extract of turmeric per daily intake, in another example from about 150 mg to about 450 mg, in another example from about 250 mg to about 400 mg, and in another example from about 300 mg to about 360 mg.

In another example, the supplement can contain rosemary (leaf). In one example, the supplement can contain a supercritical extract of rosemary. In one example, the supplement can contain from about 1 mg to about 25 mg rosemary per daily intake, in another example from about 2 mg to about 15 mg, in another example from about 3 mg to about 10 mg, and in another example from about 4 mg to about 7 mg.

The ingredients can be whole-food cultured and can be cultured and the culture media can contain probiotics and/or other nutrients. In one example, the culture media can contain organic ingredients. In one example, the media can contain ingredients selected from the group consisting of organic milled soy, *Saccharomyces cerevisiae* (organic yeast: active and inactive), organic maltodextrin, organic gum acacia, organic orange peel, organic lemon peel, organic carrot powder, organic alfalfa powder, *Lactobacilli* (*L. acidophilus, L. bifidus, L. rhamnosus*) and enzymes (deactivated), and combinations thereof. In one example, the supplement can contain all or some of the ingredients from the culture media.

The supplement can also contain flow agents. Non-limiting examples of flow agents can include gum acacia, silica, lac resin, carnauba wax, maltodextrin, and combinations thereof. In one example the gum acacia can be organic.

In one example, the dosage form can be a capsule. Each capsule can contain from about 100 mg of ingredients to about 1000 mg, in another example from about 200 mg to about 735 mg, in another example from about 250 mg to about 500 mg, and in another example from about 300 mg to about 400 mg.

In one example, the supplement can be administered as the only dietary supplement. In another example, the supplement can be administered with additional dietary supplements, such as fish oil, in particular fish oil from Wild Alaskan Salmon and/or a multivitamin and/or a supplement to support the body's healthy inflammation response and/or a supplement that supports cardio and/or a supplement that supports intestinal health. In another example, the additional supplement can be a turmeric supplement and/or a ginger supplement.

In one example, the supplement can be taken once daily. In another example, the supplement can be taken twice daily, in another example the supplement can be taken three times daily, in another example the supplement can be taken four times daily, and in another example the supplement can be taken more than four times daily. In one example, the supplement can be taken with meals. In one example, it is recommended that the supplement is taken with meals but it does not have to be taken with meals to avoid an upset stomach. In one example, the supplement can be taken in the morning, mid-day, afternoon, evening, and/or night. In one example, the supplement can be taken at the same time every day. In another example, the time the supplement is taken can vary. In one example a user administers one dosage form every time she takes a supplement, in another example two dosage, in another example three dosage forms, in another example four dosage forms, and in another example more than four dosage forms.

In one example, the daily intake can be contained in one dosage form that can be consumed once daily. In another example the daily intake can be split across more than one dosage form that can be taken either together or in another example the dosage forms can be taken throughout the day. In another example, the daily intake can be contained in two dosage forms and a user can administer two dosage forms once daily or one dosage form can be administered twice daily. In another example, the daily intake can be contained in three dosage form and a user can administer three dosage form once daily or administer one dosage form three times daily. In another example, the daily intake can be contained in four or more dosage forms that can be administered one to four times daily.

In another example, the daily intake can be contained in more than one dosage form. The dosage forms can be the same, where each dosage form has a portion of the daily intake and in another example, at least one dosage form can be different.

In one example, the supplement can be clinically proven to reduce and/or fight the appearance of fine lines and/or wrinkles, improve skin elasticity, and/or maintain a youthful appearance. In another example the supplement can contain potent antioxidant action from Astaxanthin that protects cells from damage. In another example, the supplement can contain a superfood botanical blend. In another example, the supplement can support a consumer's healthy keratin production, resulting in strong and/or healthy hair and/or nails. In another example, the supplement can contain Astaxanthin, which is a powerful antioxidant and is over 50 times more powerful/stronger than common antioxidants like Vitamin C and beta-carotene. In another example, the supplement can protect cells from damage. In another example, the supplement can provide holistic support. In another example, the supplement can support healthy aging. In another example, the supplement can help and/or support healthy immune function. In another example, the supplement can help protect cells from damage and neutralize free radicals in the body.

In one example, the supplement can be gluten free. In another example, the supplement can be vegetarian. In another example, the supplement does not contain gelatin. In another example, the supplement can be non-GMO. In one example, the supplement can be dairy-free and in another example the supplement can be free of eggs and egg products. In another example the supplement can be kosher certified and in another example the supplement can be halal certified. In another example, all or some of the supplement ingredients can be organic. In another example the supplement can be Bovine spongiform encephalopathy (BSE) free.

In one example, the dosage form can be a capsule. The capsule shell can be one-piece or two-pieces. The capsule shell can contain one or more polymers. In another example, the polymers can be vegetarian and/or non-GMO. In one example, the capsule shell can contain a polymer selected from the group consisting of hydroxypropyl methylcellulose, pullulan, and combinations thereof. In one example, the capsule shell can be substantially free of gelatin. In another example, the capsule shell can be substantially free of gelling agents and/or other ingredients. The capsule shell can also contain coloring agents, preservatives, disintegrants, lubricants and surface treatments.

EXAMPLES

Example 1

| Ingredient | Daily Intake |
|---|---|
| Biotin (from culture media) | 300 μg |
| Organic *Haematococcus pluvialis* algae (4 mg Astaxanthin) | 120 mg |
| Organic Reishi (*Ganoderma lucidum*, Ling zhi) (mycelium and fruiting bodies) | 100 mg |
| Stress and Energy Support Blend (from culture media) Organic *Schizandra* (berry), Organic Maca (root), Organic Chamomile (flower) | 75 mg |
| Digestive Support Blend (from culture media) Organic Aloe (leaf), Organic Peppermint (leaft), Organic Coriander (seed), Organic Cardamom (seed), Organic Artichoke (leaf) | 50 mg |

Other Ingredients: Capsule (pullulan [*Aureobasidium pullulans*], carrageenan, water and potassium chloride), and organic brown rice, culture media The supplement in the above example was made using standard techniques for making supplements in two-piece capsules.

Example 2—Activation of the Antioxidant Response Element

This example demonstrates the ability of an effective amount of organic astaxanthin and organic astaxanthin in combination with Digestive Support Blend (see Example 1 above), Stress and Energy Support Blend (see Example 1 above), Reishi, or biotin to synergistically activate the Antioxidant Response Element (ARE). ARE activation was quantitated using the ARE-32 reporter cell line available from CXR-Biosciences as described in the ARE Assay below.

ARE32 is a stable MCF7 cell line containing pGL8x-ARE (8 copies of the rat GST ARE linked to the luciferase gene) and pCDNA3.1, which contains the neomycin selectable marker. Selection was performed in the presence of G418 and resistant clones were isolated. Clones were screened for induction of luciferase in response to tBHQ (tert-Butylhydroquinone).

Reagents and Instruments used in this example are provided below.

Dulbecco's Modified Eagle Medium (DMEM) (Gibco™, Cat #11054-020, lot#1361242)
Fetal Bovine Serum Heat Inactivated (FBS) (Gibco™, Cat #16140-063, lot#1345764)
Geneticin G418 sulphate (G418) (Gibco™, Cat #11811-031)
Steady Glo System (Promega, Cat # E2510)
96-well plate (Costar, Cat #3917)
Penicillin-Streptomycin (Gibco™, Cat #15070-063, Lot #109733)
Tert-Butylhydroquinone (tBHQ) (Aldrich®, Cat #11, 294-1)
PerkinElmer™ EnVision™ reader
Maintenance of AREC32 Cells It is to be appreciated that equivalent reagents and instruments may be substituted for those shown, as long as the substitution does not alter the results of the assay.

The ARE32 cells are maintained routinely in the DMEM (phenol red free) containing: 10% FBS, 50 units/ml penicillin & 50 μg/ml streptomycin, 0.8 mg/ml G418. Cells are subcultured every 3-4 days. Cells were frozen in medium that contains 90% FBS and 10% dimethyl sulfoxide (DMSO).

Induction of Luciferase with Treatments and tBHQ (Positive Control):

In a 96 well-plate, seed $1 \times 10^4$ cells/well in 100 μl DMEM containing 50 units/ml penicillin, 50 μg/ml streptomycin, 0.8 mg/ml G418 and 10% FBS. Next, incubate the cells at 37° C. in a 5% $CO_2$ incubator for 24 hrs, and then replace the medium with 100 μl fresh media. Treat with test compounds at 2 μl per well, positive control was 25 μM TBHQ. (10 mM tBHQ of stock solution freshly prepared in DMSO). Add 100 μl of media after treatment for a final assay volume of 200 μL. Incubate the cells at 37° C. in $CO_2$ incubator for another 24 hours. Assay for luciferase activity with Steady-Glo® Luciferase Assay System (available from Promega, Madison, Wis., USA) by following the manufacture's instruction.

A general schematic for how the ARE reporter assay operates to identify agents that promote transcription off the ARE is described in U.S. Publication No. 2011/0262570.

As shown in Table 1 and FIG. 1, all of the components activate Nrf2. Greater activation was seen when organic astaxanthin was combined with Digestive Support Blend, Stress and Energy Support Blend, Reishi, or biotin, as compared to when any component was assayed individually.

TABLE 1

| | ARE - Fold Over Control | Standard Deviation |
|---|---|---|
| Organic Astaxanthin | 2.65 | 0.3 |
| Digestive Support Blend | 1.82 | 0.15 |
| Organic Astaxanthin + Digestive Support Blend | 3.1 | 0.24 |
| Stress and Energy Support Blend | 2.1 | 0.17 |
| Organic Astaxanthin + Stress and Energy Support Blend | 3.23 | 0.19 |

TABLE 1-continued

|  | ARE - Fold Over Control | Standard Deviation |
|---|---|---|
| Reishi | 1.84 | 0.16 |
| Organic Astaxanthin + Reishi | 2.98 | 0.21 |
| Biotin | 1.71 | 0.13 |
| Organic Astaxanthin + Biotin | 3.23 | 0.14 |

Example 3—Reduction in Level of ATP Depletion

This Example demonstrates the reduction in ATP depletion caused by Reactive Oxygen Species (ROS). Hydrogen peroxide is a well-known ROS and is commonly used as a model to analyze the effects of various ROS. In this test, keratinocytes were cultured (passage <8) in T150 flasks using EpiLife® medium (Calcium Free and Phenol Red Free, supplemented with penicillin/streptomycin and keratinocytes growth supplement, Invitrogen™ cat# MEPICF-PRF500). The keratinocytes were then plated in 24 well plates, 40,000 cells/well, 1 ml media. After 24 hours, the keratinocytes were treated with organic astaxanthin and astaxanthin in combination with Digestive Support Blend (see Example 1 above), Stress and Energy Support Blend (see Example 1 above), Reishi, or biotin for 1 hour. The keratinocytes were washed in PBS and ATP levels were measured using the CellTiter-Glo® Luminescent Cell Viability Assay (available from Promega, cat# G7571/2/3) per manufacturer's directions. Luminescence was measured on a SpectraMax® M3 (available from Molecular Devices, Sunnyvale, Calif., USA). Net luminescence (or net ATP) is calculated by subtracting the luminescence counts from the vehicle control from the luminescence counts from the treatment groups.

Figure 2:
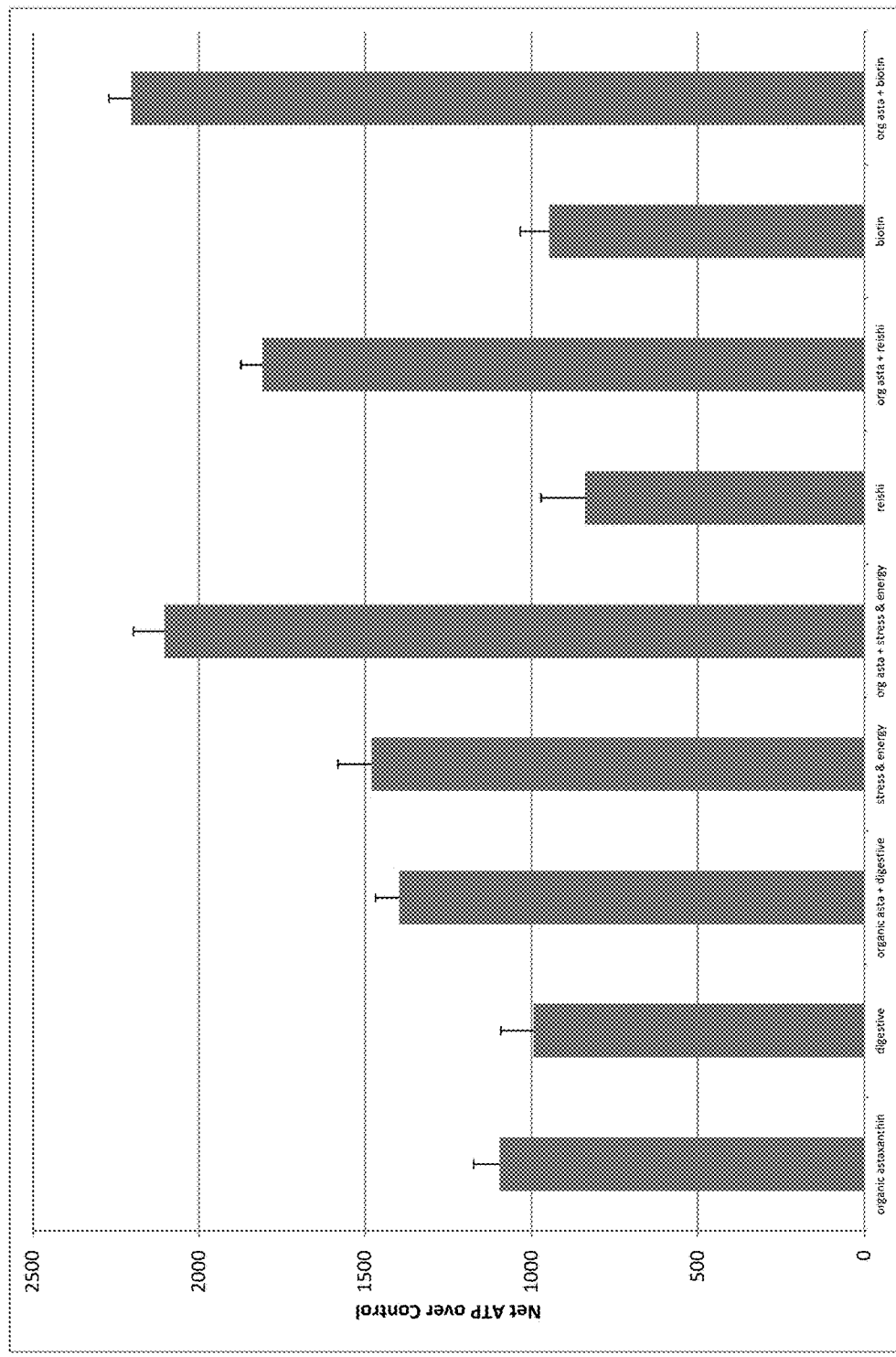
FIG. 2 shows net ATP of different components and combinations of components after peroxide stress.

As shown in Table 2 and FIG. 2, all of the components have an increase in net ATP after peroxide stress with treatment of the components. Greater net ATP was seen when organic astaxanthin was combined with Digestive Support Blend, Stress and Energy Support Blend, Reishi, or biotin, as compared to when any component was assayed individually.

|  | Net ATP | Standard Deviation |
|---|---|---|
| Organic Astaxanthin | 1096 | 98 |
| Digestive Support Blend | 994 | 72 |
| Organic Astaxanthin + Digestive Support Blend | 1397 | 103 |
| Stress and Energy Support Blend | 1480 | 94 |
| Organic Astaxanthin + Stress and Energy Support Blend | 2103 | 132 |
| Reishi | 840 | 65 |
| Organic Astaxanthin + Reishi | 1809 | 87 |
| Biotin | 947 | 67 |
| Organic Astaxanthin + Biotin | 2203 | 145 |

Example 4—PGE2 Assay

This Example demonstrates the reduction of PGE2 from UVB stressed keratinocytes with astaxanthin, biotin, and a combination. Telomerized human keratinocytes are propgated in EpiLife® Media in $CO_2$-incubator at 37° C. in T150 flasks (available from Corning®, Corning, N.Y., USA). When cell confluency reached approximately 80%, the cells were removed from the flasks using trypsin/EDTA and plated out in 24-well clear multiwall plates (available from Corning®) at a cell seeding of 40,000 cells/well. The plates were incubated another 2 days until cell confluency reaches >80%. At this point, the cells were irradiated with a Bio-Sun™ UV with UVB light for a dose of 15 mJ/cm². The media was then switched with fresh medium prepared with the treatments. The cells were then incubated for 24 hours before harvest. At harvest, the media supernatant was collected and transferred to a deep well plate and frozen in −80° C. for later determination of PGE2 levels. PGE2 levels were measured from the media supernatants using the PGE2 Assay kit (available from Cisbio™, Bedford, Mass.) per manufacturer's directions. PGE2 levels here were normalized to the ATP measurements such that the final PGE2 values were recorded as PGE2 (pg/mL)/ATP level treatment compared to control. Typically, each data point is the average of 4 replicates.

Figure 3:
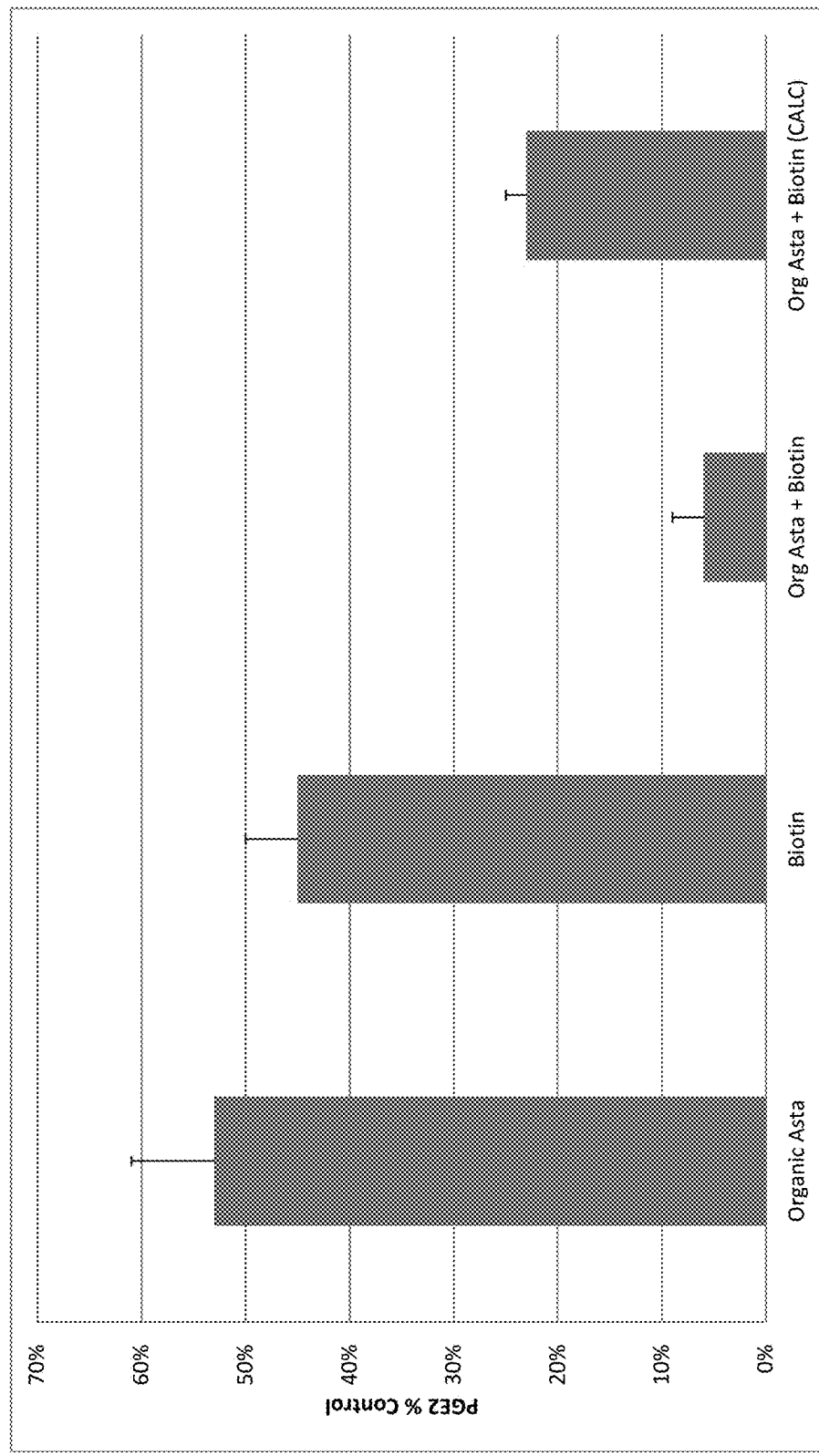
FIG. 3 shows that organic astaxanthin and biotin and combinations reduce PGE2 from UVB stressed keratinocytes.

As shown in FIG. 3, organic astaxanthin and biotin synergistically reduce PGE2 release from keratinocytes. In FIG. 3, the bar to all the way to the right shows the calculated PGE2 release from keratinocytes and the bar to the left, showing what actually happened when organic astaxanthin and biotin were used in the assay, is significantly lower.

Combinations

A. A supplement composition formulated to support the health of a human's hair skin and nails comprising a daily intake comprising: (a) about 225 µg to about 750 µg biotin; (b) about 75 mg to about 250 mg *Haematococcus pluvialis* algae wherein the *Haematococcus pluvialis* algae comprises at least 4 mg astaxanthin per daily intake; (c) about 50 mg to about 500 mg Reishi.

B. A supplement composition formulated to support the health of a human's hair skin and nails comprising a daily intake comprising: (a) at least 300 µg of biotin per daily intake; (b) at least 120 mg of *Haematococcus pluvialis* algae per daily intake; (c) and at least 100 mg Reishi.

C. The supplement composition of paragraphs A-B comprising from about 290 µg to about 500 µg biotin.

D. The supplement composition of paragraphs A-C comprising from about 100 mg to about 160 mg *Haematococcus pluvialis* algae per daily intake.

E. The supplement composition of paragraphs A-D wherein the *Haematococcus pluvialis* algae and the Reishi are organic.

F. The supplement composition of paragraphs A-E comprising from about 80 mg to about 150 mg Reishi.

G. The supplement composition of paragraphs A-F wherein the *Haematococcus pluvialis* algae comprises at least 4 mg astaxanthin per daily intake.

H. The supplement composition of paragraphs A-G further comprising at least about 75 mg of a botanical blend for stress and/or energy support comprising schizandra, maca, and chamomile.

I. The supplement composition of paragraph H wherein the botanical blend for stress and/or energy support is cultured.

J. The supplement composition of paragraphs A-I further comprising at least 50 mg of a botanical blend for digestive for digestive support comprising aloe, peppermint, coriander, cardamom, and artichoke.

K. The supplement composition of paragraph J wherein the botanical blend for stress and/or energy support is cultured.

L. The supplement composition of paragraphs A-K wherein the Reishi comprises fruiting bodies and mycelium.

M. The supplement composition of paragraphs A-L wherein the supplement is a capsule.
N. The supplement composition of paragraphs A-M wherein the supplement is vegetarian, non-GMO, and gluten free.
O. A method for reducing the appearance of fine lines and/or wrinkles by orally administering the composition of paragraphs A-N.
P. A method for maintaining a youthful appearance by orally administering the composition of paragraphs A-N.
Q. A method for improving skin elasticity by orally administering the composition of paragraphs A-N.
R. A method of protecting cells from damage by orally administering the composition of paragraphs A-N.
S. A method for supporting healthy aging by orally administering the composition of paragraphs A-N.
T. A method for supporting healthy immune response by orally administering the composition of paragraphs A-N.

Values disclosed herein as ends of ranges are not to be understood as being strictly limited to the exact numerical values recited. Instead, unless otherwise specified, each numerical range is intended to mean both the recited values and any real numbers including integers within the range. For example, a range disclosed as "1 to 10" is intended to mean "1, 2, 3, 4, 5, 6, 7, 8, 9, and 10" and a range disclosed as "1 to 2" is intended to mean "1.1, 1.2, 1.3, 1.4, 1.5, 1.6, 1.7, 1.8, 1.9, and 2."

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A capsule comprising a flow agent and a supplement composition formulated to support the health of a human's hair, skin, and nails comprising a daily intake comprising:
   a. about 225 μg to about 750 μg biotin;
   b. about 75 mg to about 250 mg *Haematococcus pluvialis* algae wherein the *Haematococcus pluvialis* algae comprises at least 4 mg astaxanthin per daily intake;
   c. about 50 mg to about 500 mg Reishi;
   d. at least about 75 mg of a botanical blend for stress and/or energy support comprising schizandra, maca, and chamomile; and
   e. at least 50 mg of a botanical blend for digestive support comprising aloe, peppermint, coriander, cardamom, and artichoke.

2. The capsule of claim 1 comprising from about 290 μg to about 500 μg biotin.

3. The capsule of claim 2 comprising from about 300 μg to about 400 μg biotin.

4. The capsule of claim 2 comprising from about 100 mg to about 160 mg *Haematococcus pluvialis* algae per daily intake.

5. The capsule of claim 4 comprising from about 80 mg to about 150 mg Reishi.

6. The capsule of claim 5 comprising from about 90 mg to about 120 mg Reishi.

7. The capsule of claim 6 wherein the Reishi comprises fruiting bodis and mycelium.

8. The capsule of claim 1 wherein the *Haematococcus pluvialis* algae and the Reishi are organic.

9. The capsule of claim 1 wherein the supplement is vegetarian, non-GMO, and gluten free.

* * * * *